Figure 1:
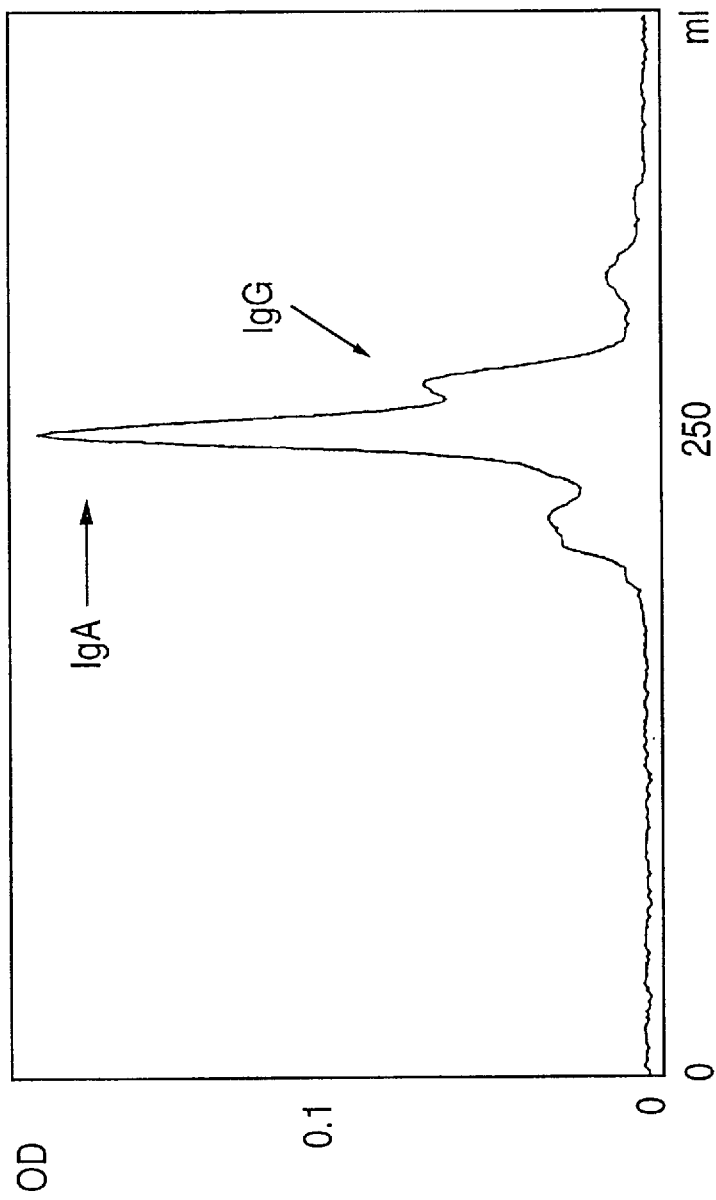

United States Patent [19]
Mannhalter et al.

[11] Patent Number: 5,808,000
[45] Date of Patent: Sep. 15, 1998

[54] VIRUS-SAFE MONOMERIC HUMAN IMMUNOGLOBULIN A AND METHODS FOR ITS PRODUCTION

[75] Inventors: Josef W. Mannhalter; Heinz Leibl; Martha Eibl; Regine Tomasits; Hermann Wolf, all of Vienna, Austria

[73] Assignee: Immuno Aktiengesellschaft, Vienna, Austria

[21] Appl. No.: 500,161

[22] Filed: Jul. 10, 1995

[30] Foreign Application Priority Data

Jul. 14, 1994 [DE] Germany .......................... 44 24 935.7

[51] Int. Cl.$^6$ .................................................. C07K 16/00
[52] U.S. Cl. ................... 530/387.1; 530/389.1; 435/5; 436/513; 436/547
[58] Field of Search .............. 435/5; 530/387.1, 530/389.1; 436/513, 547

[56] References Cited

U.S. PATENT DOCUMENTS

| | | | |
|---|---|---|---|
| 4,186,192 | 1/1980 | Lundblad et al. | 424/85 |
| 5,258,177 | 11/1993 | Uemura et al. | 424/85.8 |
| 5,371,196 | 12/1994 | Yuki et al. | 530/390.1 |

FOREIGN PATENT DOCUMENTS

| | | |
|---|---|---|
| 2063872 | 9/1992 | Canada . |
| 0 131 740 | 1/1985 | European Pat. Off. . |
| 0 159 311 | 10/1985 | European Pat. Off. . |
| 0 050 061 | 12/1985 | European Pat. Off. . |
| 0168506A1 | 1/1986 | European Pat. Off. . |
| 0 177 836 | 4/1986 | European Pat. Off. . |
| 0196761A2 | 10/1986 | European Pat. Off. . |
| 0 247 998 | 12/1987 | European Pat. Off. . |
| 0352500A3 | 1/1990 | European Pat. Off. . |
| 0 506 651 | 9/1992 | European Pat. Off. . |
| CH684164A5 | 7/1994 | Germany . |
| 44 34 538 | 4/1995 | Germany . |
| 57-59815 | 4/1982 | Japan . |
| 925764 | 4/1993 | South Africa . |
| 2030150 | 4/1980 | United Kingdom . |

OTHER PUBLICATIONS

Mazanec, et al., *Virus Research*, vol. 23, No. 1–2, pp. 1–12, 1992.
Hutchens, et al. *J. Immunol. Methods*, vol. 128, pp. 89–99, 1990.
Gregory, *Lab. Med.*, vol. 25, No. 11, pp. 724–728, 1994 (abstract only).
Heremans, "Immunoglobulin A in: The Antigens", vol. 2:365–522, Academic Press, New York, (1974).
Collard et al., "Isolation And Purification of Bovine Immunoglobulins: Use of Sephacryl S–300 Filtration Avoids Protein Precipitation Steps", *Ann. Rech. Vet.*, vol. 15:497–501, (1984).
Pattison et al., "Elution Patterns Of Rubella IgM, IgA, Antibodies From A Dextran And An Agarose Gel", *J. Clin. Path.*, vol. 28:670–673, (1975).
Wells et al., "Inactivation And Partition of Human T–Cell Lymphotrophic Virus, Type III, During Ethanol Fractionation of Plasma", *Transfusion*, vol. 26(2):210–213, (1986).
Mancini et al., "Immunochemical quantitation of Antigens By Single Radial Immunodiffusion", *Immunochemistry*, vol. 2:235–254, (1965).
Ouchterlony, "Antigen—Antibody Reactions in Gels", *Acta Path. Microbiol. Scand.*, vol. 26:507–515, (1949).
Laemmli, "Cleavage of Stuctural Proteins During The Assembly of The Head of Bacteriophage T4", *Nature*, vol. 227:680–685, (1970).
H. Leibl, et al., "Isolation of Human Serum IgA Using Thiophilic Adsorption Chromatography", *Protein Expression and Purification* 6: 408–410 (1995).
Schiff et al. J. Allergy Clin. Immunol. 88(1): 61–67 (1991).

*Primary Examiner*—Toni R. Scheiner
*Attorney, Agent, or Firm*—Foley & Lardner

[57] ABSTRACT

A virus-safe monomeric human IgA is described which is essentially free of IgG. The IgA according to the invention is obtainable according to a process in which (a) an IgA-containing fraction is subjected to a purification such that a monomeric IgA which is essentially free of IgG is obtained and (b) the obtained product is subjected to a process for the inactivation of viruses.

30 Claims, 11 Drawing Sheets

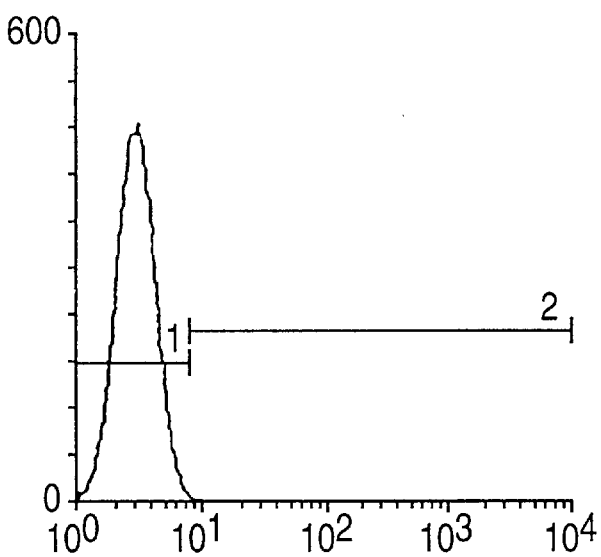
FIG. 7A  E. COLI COATED WITH PBS (BLANK)
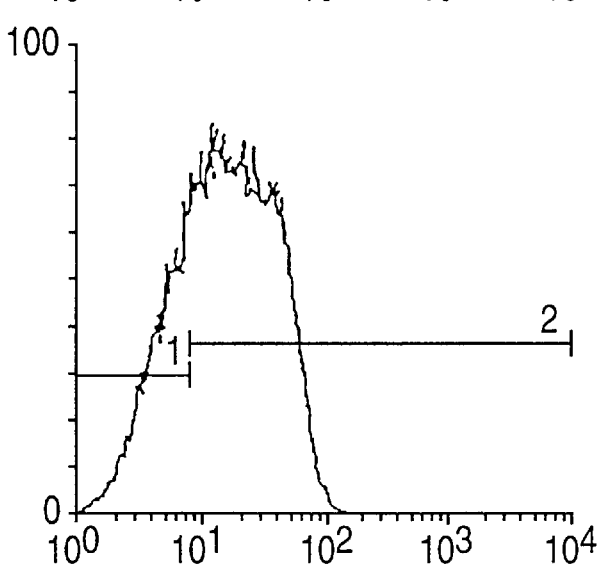
FIG. 7B  E. COLI COATED WITH IgA FROM EXAMPLE 3
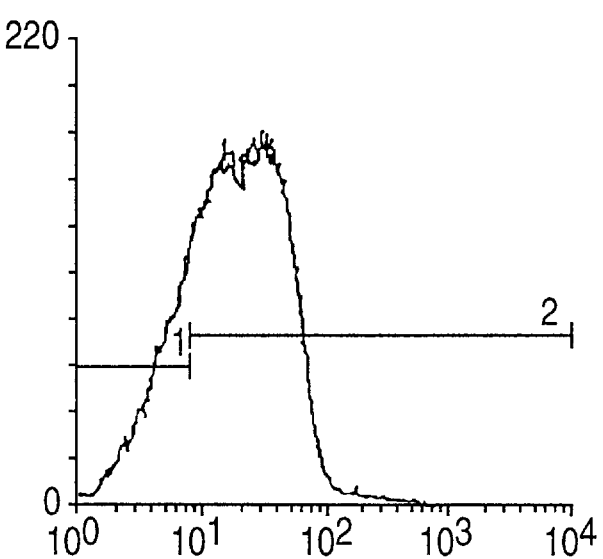
FIG. 7C  E. COLI COATED WITH PLASMA POOL

VIRUS-SAFE MONOMERIC HUMAN IMMUNOGLOBULIN A AND METHODS FOR ITS PRODUCTION

The invention relates to a virus-safe monomeric human immunoglobulin A (IgA), a method for its production and stable pharmaceutical preparation containing this.

Immunoglobulins (Ig) are specific immune competent proteins in blood, lymph and in other body secretions of all vertebrates. The immunoglobulins are synthesized by B-lymphocytes. The monomeric immunoglobulins each consist of two L (light) and H (heavy) chains which are linked by disulfide bridges. The immunoglobulins are glycoproteins which function as antibodies and whose secretion is induced by antigens. Quantitatively, they constitute approximately 20% of the total plasma proteins. Up to now, 5 main classes of immunoglobulins have been identified in humans (IgA, IgD, IgE, IgG, IgM), which differ in their H chains, serum concentration, molecular weight (ca. 146,000 to 970,000), carbohydrate content, electrophoretic mobility and in their biological properties. The main classes IgA and IgG can be further divided into subclasses (for example, IgA1 and IgA2). The diversity of the immunoglobulin classes and subclasses as well as their diverse different specificities in the binding of antigens is accomplished by combination of various present genes. Active immunization is based on the induced secretion of immunoglobulins, whereas, in passive immunization against various viral and bacterial infections, immunoglobulins are supplied.

Immunoglobulin A (IgA) represents the main antibody class in external secretions such as saliva, lachrymal fluid and the mucous secretion of the bronchial and intestinal tracts. Therewith, immunoglobulin A serves as one of the first defense lines against bacterial and viral antigens.

For the prophylaxis and treatment of bacterial and viral infections, pharmaceutical compositions based on immunoglobulins, for example immunoglobulin A, have already been proposed and used (see for example JP-A-57-59815).

IgA can be transported by a receptor, the secretory component, from the blood side through the epithelial cells to the extracellular side.

In the pure monomeric form, IgA consists of two light (L) and two heavy (H) chains; in the dimeric secretory form, two such monomers are linked by the so-called J-chain (joining chain). In the secretions of the mucous membranes and glands, dimers with an additional secretory component (so-called SC component) are mainly present.

In solution, IgA is present as IgA monomer in equilibrium with IgA dimer. In this equilibrium, the portion of dimeric IgA maximally amounts to about 25% of the total IgA.

IgA consists of two subclasses, IgA1 and IgA2 which are present in a native ratio of about 80% by weight to 20% by weight. This ratio can change in the course of isolation. The native ratio of kappa to lambda light chains in an immunoglobulin preparation, measured in U/dl, amounts to about 1:1

IgA represents only ca. 3–4% of the total proteins from normal human serum. Because IgA has a pronounced tendency to complex formation and aggregation during purification, the isolation of monomeric IgA from serum usually gives low yields, and among the numerous purification procedures, only few are known which are also suitable for a large scale production.

Main impurities of the IgA preparations are the various subclasses of immunoglobulin G, which have to be removed and thus require purification methods which further reduce the yield of IgA.

Known and popular methods for the purification of immunoglobulins are mostly based on differences in physical properties, e.g. different solubility in aqueous systems (purification by fractionated precipitation), dissimilarities in charge (purification by ion exchange chromatography) or differences in the molecular size (purification by molecular exclusion chromatography)

In JP-A-57-59815, a purification of immunoglobulins from human starting material is described. According to this, precipitation with ammonium sulfate is followed by a gel filtration on Sephacryl® S-200 and, subsequently, an affinity chromatography for the separation from IgG. Based on the very similar molecular weights of monomeric IgA and IgG (IgA: 162 kD, IgG: 153 kD, see J. F. Heremans, Immunoglobulin A in: The Antigens, vol. 2 [1974], pages 365–522; Academic Press, New York), isolation of monomeric IgA is however difficult. Although the purified IgA is used as an active component in pharmaceutical compositions, and human starting material is employed for purification, no methods for the inactivation of viruses are described in JP-A-57-59815. Moreover, the IgA is present in capsules or pellets which can not be subjected to methods for the inactivation of viruses, and especially can not be heat treated.

A. Collard et al., Ann. Rech. Vet. 15 (4) (1984) 497–501 describe a purification of the immunoglobulins A, G and M from bovine serum or colostrum by means of gel filtration on Sephacryl® S-300. However, the yield is low and moreover the end product is contaminated with IgG1 and IgG2 subclasses; additionally a separation between IgA and IgG from serum samples is less successful than from colostrum. In colostrum IgA is present as secretory IgA which consists of a complex of IgA dimers and additional protein chains, and the high molecular mass of the complex facilitates separation by gel exclusion chromatography.

According to J. R. Patterson et al., J. Clin. Path. 28 (1975) 670–673, two different gel filtration mediums, namely Sephadex® G-200 and Bio-Gel® A-5M, are used for the separation of immunoglobulins from sera. The IgA fraction obtained in this manner does not comprise a monomeric IgA preparation, but instead, an IgA preparation with high molecular weight.

A major problem in using human starting material for the production of immunoglobulins is, however, the virus saftey of the obtained products. Despite donor selection and testing of the individual donor plasmas, it can not be ruled out that based on the low sensitivity of some tests, infectious pathogenic agents, especially hepatitis viruses or retroviruses such as HIV, are still present in the donor pool.

Although the production of an immunoglobulin preparation by fractionated alcohol precipitation according to Cohn results in depletion/inactivation of viruses of more than $10^{15}$ units (see for example Wells et al., Transfusion 26 (1986) 210–213), the danger of an insufficient virus inactivation, i.e. an insufficient virus safety, still exists, especially when a new purification method is employed.

In order to obtain a sufficient inactivation of viruses, a heat treatment can be carried out for example. As opposed to other processes for the inactivation of viruses, e.g. a treatment with a solvent/detergent system according to EP-B-0131740, the heat treatment has the advantage that non-lipid coated viruses, e.g. hepatitis A viruses, are also inactivated.

However, a disadvantage of the heat treatment, and also of other processes for the inactivation of viruses, is that a substantial portion of IgA can be multimerized and/or polymerized.

In popular processes for the inactivation of viruses and especially in the heat treatment, an aggregate formation of the immunoglobulins must be expected. However, aggregates of this type cause, among others, an increase of the anticomplimentary activity and therewith incompatibility reactions after intravenous administration. Therefore, some purification methods which include a step for the inactivation of viruses or especially a heat treatment are preformed in the presence of stabilizers.

A heat treatment in the presence of stabilizers is described for example in EP-B-0177836, according to which, a lyophilized immunoglobulin G with a moisture content of 3% or less is heated to 30° C. to 100° C. under addition of a stabilizer for 10 minutes to 200 hours. The stabilizer protects the relatively labile immunoglobulins from denaturation and maintains therewith their biological activity.

A disadvantage of the heat treatment in the presence of stabilizers is the presence of these stabilizers in the end product which must subsequently be removed.

A heat treatment without stabilizers is described for example in EP-B-0159311. According to this, the blood products are heated in a moist (between 5 and 70% water content) solid state during a second to 100 hours. Instead of water also hydroxyl group-containing compounds, for example methanol, ethanol or mannitol can also be used.

The object of the present invention is to make available a virus-safe monomeric human immunoglobulin A (IgA) which is essentially free of immunoglobulin G (IgG). The product is to be obtained by a simple and safe procedure which avoids the above problems demonstrated in connection with the prior art. This object is solved with the subject matter of the present invention.

Subject matter of the invention is a virus-safe monomeric IgA according to patent claim 1 which is essentially free of IgG and is obtainable by purification of an immunoglobulin-containing fraction and carrying out a process for the inactivation of viruses.

Preferred embodiments include those where purification is done by chromatographic procedures, such as gel permeation chromatography and/or thiophilic chromatography. Inactivation of viruses can be performed by heat treatment. The monomeric IgA can comprise IgA1 and IgA2 in a native composition. Furthermore, the monomeric IgA can be free of at least one of fibrinogen and plasminogen.

Further subject matter is a stable pharmaceutical composition (stable pharmaceutical preparation) including those described above which contains a fraction of human monomeric IgA that is essentially free of IgG.

Preferred embodiments include those that consist essentially of IgA, and can contain pharmaceutically acceptable adjuvants and additives.

Further subject matter of the invention is a method for producing virus-safe monomeric IgA, comprising purifying an immunoglobulin containing fraction to obtain monomeric IgA that is essentially free of IgG, and then treating the IgA to inactivate any contaminating viruses.

Suitable embodiments include those where purification is done by chromatographic procedures, such as gel permeation chromatography and/or thiophilic chromatography. Inactivation of viruses can be performed by heat treatment. The immunoglobulin containing fraction can be from human serum, human plasma, human plasma fractions, human colostrum, the Cohn II and III fractions. The fraction can be pre-purified.

If gel permeation chromatography is used, it can employ hydrophilic/hydrophobic interactions and/or electrostatic interactions, and can employ SUPERDEX media. Affinity chromatopraphy can be used to provide additional purification. Heat treatment to inactivate viruses is usually done at 40° C. to 80° C., preferably at 50° C. to 65° C. Prior to heat treatment, the preparation can be dialyzed against water.

According to the method of the invention it is surprisingly possible to obtain an IgA which is essentially free of IgG, is present as a monomeric IgA and can be considered virus-safe, i.e. the infection with viruses after use of this product can be excluded.

By monomeric IgA, according to the invention, an IgA preparation is understood which contains at least 96% by weight monomeric IgA with respect to the total amount of IgA.

This prejudice is based on the high tendency of immunoglobulins to form aggregates following treatment with chemical substances used in processes for the inactivation of viruses or heat treatment. Up to now a prejudice existed against a treatment for the inactivation of viruses and especially for a heat treatment. Surprisingly, it has now been found according to the inventive method that IgA is not subject to aggregate formation by carrying out a process for the inactivation of viruses according to process step (b), also when for example a heat treatment is carried out without addition of customary stabilizers, such as for example carbohydrates or amino acids. A preferred embodiment of the invention designates a heat treatment, and especially a heat treatment in solution, wherein polyethylene glycol in a non-precipitating amount is present for the improvement of the virus inactivating effect. For this, the use of low molecular weight PEG is preferred.

The human IgA containing starting material employed in the method according to the invention is preferably serum, plasma and/or plasma fractions of human origin.

Suitably, the plasma and/or plasma fractions are treated with alcohol according to the method of Cohn, and the Cohn II+III fractions are employed.

The IgA-containing starting material is preferably purified by means of a chromatographic method; particularly gel permeation chromatography and/or thiophilic chromatography is preferably applied. The IgA-containing starting material can also be pre-purified, for example by precipitation with ethanol, polyethylene glycol and/or ammonium sulfate, and/or by a further chromatographic method, e.g. use of an ion exchanger, adsorption to hydroxyapatite and/or dextran sulfate and/or purification on heparin Sepharose®. Further purification methods comprise a precipitation of contaminated proteins with $ZnSO_4$ or Rivanol®. By performing such a pre-purification, the chromatography material used in subsequent steps, for example the gel employed in gel permeation chromatography, can be preserved. Thereby, a longer use of the chromatography columns can be obtained, for which reason the method is also particularly suitable for use in a large technical scale.

For the separation of IgG dimers, additional affinity chromatography is preferably carried out, for example on immobilized Protein A or G, or on anti-IgG antibodies which are coupled on a solid matrix.

This additional affinity chromatography can be carried out before the method step (a), between the method steps (a) and (b) and/or after the method step (b); most appropriately, it is carried out before or after the chromatographic purification.

For carrying out a method according to step (b), the product obtained in the previous steps is suitably employed in dissolved or solid form. For heat treatment in solid form, the product to be submitted to the heat treatment preferably has a moisture content of 5 to 70% by weight. In another preferred embodiment a lyophilizate is employed in solid form. If a heat treatment is carried out according to step (b), this preferably is performed at a temperature between 40° C. and 80° C., and especially between 50° C. and 65° C. The heat treatment is thereby carried out at least for a time period sufficient for the inactivation of viruses, and preferably for a time period between 30 minutes to 10 hours. Preferably, the heat treatment is performed as a steam treatment, and especially according to a method described in EP-A-0159311.

However, aside from heat treatment, all other methods for the inactivation of viruses can also be used. Thus, for example, a solvent/detergent treatment according to EP-131 740 or a detergent treatment according to EP- 50 061 can be applied. Methods which comprise a UV irradiation together with β-propiolactone as a process for the inactivation of viruses are also suitable.

As further methods to subject immunoglobulin-containing fractions to a method for the inactivation of infectious agents, chemical or physical treatments in the presence of a polyether as described in DE-44 34 538 are useful. As polyether, polyhydroxyether, as for example polyalkylene glycol and especially polyethylene glycol and polypropylene glycol can be employed for this purpose.

As a further possibility for the inactivation of pathogenic agents, the use of neutral peptide hydrolases, such as for example trypsin or chymotrypsin, according to EP-247 998 should be mentioned.

It can also be suitable to combine the heat treatment with one or several other methods known and customary for virus inactivation, and especially with UV irradiation, treatment with tensides, and/or treatment with a solvent/detergent system. Thereby, the individual steps can be performed simultaneously (for example heat treatment with simultaneous UV irradiation) or in any other order.

By a combination of heat treatment with one or several other methods for virus inactivation, the various mechanisms of action functional in these different inactivation procedures can be employed, whereby the virus safety of the product can be further increased.

Before heat treatment, dialysis against water can also be suitably carried out. This dialysis has the advantage to remove for the most part contaminants still present in the preparation. In addition, stabilizing substances employed, if applicable, or being present in the preparation can be removed as well.

If gel permeation chromatography is carried out according to method step (a), the separation of molecules is based on their different molecular size with the gel functioning as a molecular sieve. Thus, gel permeation chromatography is therefore normally independent of the ionic strength applied. As materials for gel permeation chromatography, customary gel permeation chromatography matrices can be employed, for example Superose®. Sephacryl®, Sepharose® or Sephadex®.

In the method according to the invention, it has been surprisingly demonstrated that separation of the IgG from monomeric IgA on some matrices used for gel permeation chromatography is also dependent on the ionic strength. It is to be concluded that in such cases additional hydrophobic/hydrophilic and/or electrostatic interactions between the substances to be separated and the gel matrices may play a role.

Therefore according to the invention, hydrophobic/hydrophilic and/or electrostatic gel permeation chromatography is preferably performed with a matrix that simultaneously has a hydrophobic/hydrophilic and/or electrostatic interaction and affinity effect. Therewith an excellent separation of IgG and IgA results which is surprisingly better than use of a customary material named above for gel permeation chromatography.

Preferably, for the gel permeation chromatography according to the invention, a gel of cross-linked agarose as it is employed for fast protein liquid chromatography (FPLC®) of biomolecules is employed, such as for example Superdex® or Superose® (both from Pharmacia) or a gel of a synthetic material is used.

Instead of gel permeation chromatography, thiophilic chromatography can also be carried out, and the combination of both purification methods is also possible. Suitable adsorbents for thiophilic chromatography are preferably so-called T gels based on carbohydrates or synthetic carrier materials which contain structures such as R—$SO_2$—$CH_2$— or R—S—$CH_2$—$CH_2$—$SO_2$— and are directed against sulfur-containing structures of the protein.

The adsorption of plasma or a plasma fraction on a thiophilic matrix and the subsequent elution of a fraction containing monomeric IgA also represents a suitable method for the production of a monomeric IgA-containing preparation.

As virus-safe monomeric human IgA, one essentially free of IgG is produced and used.

"Essentially free of IgG" means that the portion of IgG in the total immunoglobulin amounts to less that 10% by weight, and preferably less than 5% by weight, and especially less than 3% by weight.

Preferably, the monomeric IgA is also essentially free of IgG dimers. "Essentially free of IgG dimers" means therewith that the portion of IgG dimers in the total immunoglobulin is smaller than 5% by weight, and preferably smaller than 3% by weight, and especially is under the detection limit of radial immunodiffusion (RID).

The virus-safe monomeric human IgA produced and used according to the invention is also preferably free of fibrinogen and/or plasminogen. Free of fibrinogen and/or plasminogen means therewith that these contaminants are not detectable with common tests, such as for example by means of radial immunodiffusion (RID), coagulation tests or fibrinolysis tests. In this manner, it is ensured that no material which could additionally burden the organism by the administration of the immunoglobulin is present in the preparations according to the invention and pharmaceutical compositions containing these.

In the IgA produced and used according to the invention, the subclasses IgA1 and IgA2 are preferably present in a ratio that corresponds to the composition of native IgA.

Subject matter of the present invention is also a pharmaceutical preparation which contains a virus-safe monomeric human IgA according to the invention, optionally together with customary pharmaceutical carriers and/or diluents.

By using the IgA which can be produced according to the invention, it is possible to make available a pharmaceutical composition which is stable and virus-safe and which can also additionally be heat treated.

The pharmaceutical composition can, aside from the IgA, also contain other active components (active ingredients), as long as they are compatible with IgA and are suitable and useful for the purpose of the pharmaceutical composition.

The pharmaceutical compositions according to the invention are especially suitable for the prevention and treatment of inflammations, infections and/or allergies.

As pharmaceutical carriers and diluents, customary pharmaceutical acceptable carriers and diluents can be used.

The production of the pharmaceutical compositions is performed according to known and customary methods and is especially dependent on the mode of the intended administration.

The administration of IgA can be carried out in local, mucosal, for example oral, or systemic ways.

The dosage depends on the administration mode and the frequency of the administration as well as the extent and the severity of the disorder, for example inflammation. When high total doses of IgA are administered it is often preferable to administer the IgA in several smaller dosage amounts. These considerations in view of the dosage and the administration mode are generally known to the skilled person in this field.

For example, IgA can be given orally (normally 1 to 10 g/day or more in severe cases) preferably in 3 or more doses.

Typically, IgA can be administered systemically for example by means of intravenous injections, continuous infusion or both. Typically, 50 to 2000 mg IgA/kg/day are administered. In rare cases, the IgA can also be administered intramuscularly, normally with a dosage of ca. 50 to 100 mg IgA/kg/day.

Immunoglobulin can also be administered mucosally, for example by means of inhalations (up to 10 ml/day, 10 to 100 mg IgA/ml), or nasally (15 to 200 mg/ml) by means of sprays or drops, or by intra-articular injections (which according to need contain 1 to 5 ml of a solution of 10 to 100 mg IgA/ml). Other modes of administration include suppositories (100 to 1000 IgA/dose) and transdermal plasters. Transdermal plasters can be used for example for treating skin inflammations.

As administration forms such are particularly considered which are customary for the prevention and treatment of virus infections, and especially oral administration forms such as capsules, tablets, granulates, pellets, mini-pellets and microcapsules which, for the treatment of viral infections of the intestine, are preferably provided with a customary stomach fluid-resistant, intestine-soluble coating.

In addition, the pharmaceutical preparations can be present in an administration form suitable for parenteral administration or in the form of compositions suitable for injection or infusion.

For a prophylactic and therapeutic treatment of humans, the daily administration dose of the pharmaceutical compositions according to the invention usually amounts to 10 to 5000 mg with respect to the monomeric IgA according to the invention. However, this is also and especially determined by the general condition and age of the patient and by the severity of the disorder.

The following examples should more closely illustrate the invention without limiting the invention to the examples.

In the following, the figures relating to the examples and their meaning are given:

FIG. 1

Ex. 1

Column: Superdex® 200 HR 35/600

Preparative run for the isolation of IgA from Cohn III precipitate

FIG. 2

Ex. 1

Column: Superdex® HR 10/30

Analysis of the end product (IgA)

FIG. 3

Ex. 2

IgA: gel electrophoresis/densitometry

FIG. 4

Ex. 3

IgA: gel electrophoresis/densitometry

FIG. 5

Ex. 4

IgA: gel electrophoresis/densitometry

FIG. 6

Ex. 4

Column: Superdex® HR 10/30

IgA end product ("M" monomers, "D" dimers, "A" aggregates)

FIG. 7

Ex. 6

E. coli coated with IgA x-axis: intensity of the fluorescence y-axis: number of the bacteria detected

FIG. 8

Ex. 7

Column: Superdex® HR 10/30

IgA after lyophilization reconstituted in PBS

FIG. 9

Ex. 8

Column: Superdex® HR 10/30

IgA after heat treatment (60° C., 30 min)

FIG. 10

Ex. 8

Column: Superdex® HR 10/30

IgA after heat treatment (40° C., 8 hours)

FIG. 11

Ex. 8

Column: Superdex® HR 10/30

IgA after heat treatment (40° C., 8 hours+50° C., 8 hours)

FIG. 12

Ex. 9

Column: Superdex® HR 10/30

IgA and IgG separation with run buffer: PBS (0.15M NaCl)

FIG. 13

Ex. 9

Column: Superose® 6 HR 10/30

IgA and IgG separation with buffer: PBS (0.15M NaCl)

FIG. 14

Ex. 9

Column: Superdex® HR 10/30

IgA and IgG separation with run buffer: PBS and 2M NaCl

In all Figures presenting column chromatography runs the x-axis represents the elution volume in ml.

The following abbreviations are used:
OD . . . optical density
Hp . . . haptoglobin subunits
LC . . . light chain
HC . . . heavy chain
M . . . monomers
D . . . dimers
A . . . aggregates
PBS . . . phosphate buffered saline

EXAMPLE 1

As described in the patent application EP 0506 651, a Cohn II+III fraction is produced from human plasma and extracted with a phosphate acetate buffer. This material is mixed with ethanol at pH 5.3 and at a temperature of −2° C. to a final concentration of 12%, wherein a precipitate is formed which is separated and stored at −2° C. This paste is then treated in the following manner: 25 ml of a 0.9% NaCl solution which contains 10 μg Soya bean trypsin inhibitor (Sigma, St. Louis, Mo., U.S.A.; type I-S per ml) is added per gram of paste. The paste is suspended by stirring at 4° C. overnight, whereby a portion of the proteins is dissolved. For separation of the non-dissolved components, the suspension is centrifuged for 60 min at 18,900×g at 4° C. The precipitate is discarded. The supernatant is mixed with heparin Sepharose® CL-6B (Pharmacia-LKB, Uppsala, Sweden) and stirred overnight at 4° C. Then, the gel is separated from the supernatant over a nylon filter (85 μm mesh size). The gel is washed twice with 0.9% NaCl solution (each time with ¼ of the sample volume). Supernatant and wash fluids are combined.

The material not bound by the heparin Sepharose® CL-6B is pumped with a flow rate of 1.3 ml/min over a lysine Sepharose® 4B (Pharmacia-LKB) column (inner diameter=2.6 cm; 58 ml gel) which was previously equilibrated in a buffer consisting of 50 mM sodium phosphate+150 mM NaCl, pH 7.5. The unbound material is used for the subsequent IgA isolation.

(The plasminogen bound to the column can be eluted after a further washing step with 100 ml of a buffer consisting of 50 mM sodium phosphate, 0.5M NaCl, 0.2M epsilon-aminocaproic acid, pH 7.5)

Lipoproteins are removed from the material not bound to lysine Sepharose® by a precipitation with dextran sulfate (Sigma; sodium salt; MW: ca. 5000): to this, 0.08 ml 10% dextran sulfate solution and 1 ml 1M calcium chloride solution are added per ml of sample. The mixture is stirred for 30 min at 25° to 30° C. and subsequently centrifuged. The precipitate is discarded and to remove calcium ions the supernatant is dialyzed against the three-fold sample volume of 0.9% NaCl at room temperature using an Amicon (Beverly, Mass., U.S.A.) Spiral Module S1Y30 Cross Flow.

Solid ammonium sulfate is added to the dialyzed material under stirring to obtain a final concentration of 2M. Then, stirring continues for 30 min and subsequently the precipitate formed is centrifuged at 1540×g at 4° C. (The supernatant is discarded)

The precipitate is resuspended in phosphate-buffered isotonic saline solution, pH 7.4, (in the following abbreviated PBS) and dialyzed at room temperature against the three-fold sample volume of PBS using an Amicon Spiral Module S1Y30 Cross Flow. The dialyzed material clarified by centrifugation is separated using a hydroxyapatite column (BioRad, Richmond, Calif., U.S.A.; macro prep ceramic hydroxyapatite; 20 microns; 50 ml gel; inner diameter=2.6 cm). At a flow rate of 2 ml/min, 200 ml of sample are applied to the column equilibrated with buffer A (PBS, pH 7.4) per run. IgA binds to the hydroxyapatite and can be eluted with 140 ml buffer B (15 mM NaH$_2$PO$_4$/Na$_2$HPO$_4$) in PBS with a pH of 6.8.

The material eluted from the hydroxyapatite with buffer B is dialyzed using an Amicon Spiral Module S1Y30 Cross Flow at room temperature against the three-fold sample volume of 50 mM sodium acetate/acetic acid buffer, pH 5.0.

The dialyzed material is mixed with an anion exchanger in batch process. To this, the ion exchanger (Fractogel® EMD TMAE 650(S); particle size 0.02–0.04 mm; Merck, Darmstadt, Germany; suspended 1:2 in 50 mM sodium acetate/acetic acid buffer, pH 5.0) is added to the sample such that 2 ml of gel suspension are present per 10 mg of protein. The suspension is stirred overnight at 4° C. Unbound material is separated over a Buchner funnel and the gel is washed 2×with 50 mM sodium acetate/acetic acid buffer, pH 5.0. Subsequently, the gel is stirred for 2 hours at 4° C. with 50 mM sodium acetate/acetic acid+80 mM NaCl, pH 6.0. Then, the gel is separated from proteins by use of a Buchner funnel.

The eluted material is concentrated with an Amicon stirred cell equipped with a Diaflo ultrafiltration membrane YM30 to give a protein concentration of 10 mg protein/ml.

This material is separated according to the invention by gel filtration using a Superdex® prep grade HR 35/600 (Pharmacia-LKB) column. For each run, 10 ml of the sample are applied at a flow rate of 2.5 ml/min to the gel equilibrated in PBS, pH 7.4, and isocratically eluted. With the aid of this column, the majority of the IgG still present and other contaminants can be removed from IgA (FIG. 1 shows the gel filtration on Superdex® 200 HR 35/600). The IgA-containing fractions are collected, combined and further treated with protein G Sepharose® 4 fast flow (Pharmacia-LKB; equilibrated in PBS, pH 7.4). This affinity chromatography is carried out in batch process, wherein 1 ml of gel is employed per 50 ml of sample. The suspension is stirred overnight at 4° C. The gel is separated from the sample by centrifugation and washed 2×with PBS. Supernatant and wash solution are combined and dialyzed in a dialysis bag (Spectrapor MWCO 12,000–14,000) against distilled water.

The end product produced in this manner was analyzed:

Analysis by gel filtration is carried out on an analytical Superdex® HR 10/30 FPLC. column (Pharmacia-LKB) with PBS as a running buffer at a flow rate of 0.5 ml/min. The optical density (OD) is measured at 280 nm in a flow-through cell and recorded against the elution volume (ml).

Figure 2:
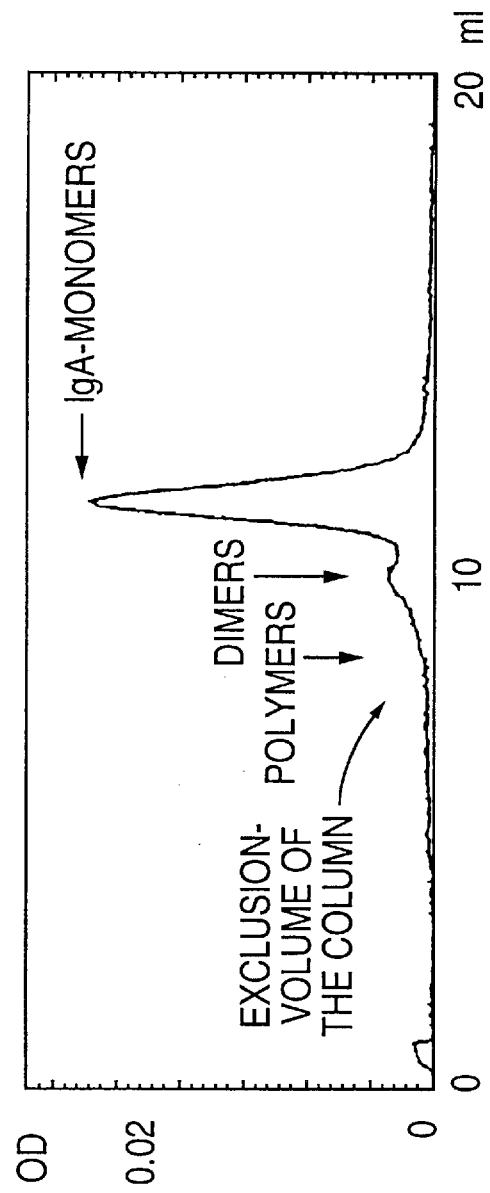

The result of this analysis depicted in FIG. 2 shows that the end product consists mostly of IgA monomers and a portion of 5–10% IgA dimers which form in solution from IgA monomers.

IgA aggregates are present at <2%. In an IgA solution concentrated to >5 mg/ml, IgG can not be detected by radial immunodiffusion which signifies, based on the sensitivity limit of the RID plate desitometry, that less than 0.025 mg/ml IgG are present. Hence, the end product produced according to the invention contains less than 1% IgG. Plasminogen and fibrinogen are also not detectable (Table 1). The yield of IgA with respect to the starting material (the NaCl extracted paste) amounts to 7 to 12%.

TABLE 1

Result of IgA purification (starting material is the paste precipitated by 12% ethanol from Cohn fraction II + III and extracted with 0.9% NaCl) IgA, IgG and plasminogen were analyzed by radial immunodiffusion (Mancini, G., Carbonara, A. O., Heremans, J. F., Immunochemistry 2 [1965] 235–254); fibrinogen is detected by the method of Ouchterlony (Acta Path. Microbiol. Scand. 26 [1949] 507–515).

|  | IgA mg/ml | IgG mg/ml | plasminogen mg/ml | fibrinogen |
|---|---|---|---|---|
| starting material | 1.3 | 1.70 | 0.41 | +++ |
| end product | 5.4 | n.d. | n.d. | n.d. | n.d. = not detectable

EXAMPLE 2

As described in Example 1, an extract is produced from the paste which is precipitated by 12% ethanol from Cohn fraction II+III by stirring in 0.9% NaCl.

The extract is precipitated by addition of solid ammonium sulfate. The final ammonium sulfate concentration of the solution is 2M. The precipitate is centrifuged for 10 min at 1540×g at 4° C. The supernatant is discarded.

The precipitate is dissolved in PBS and adjusted to the starting volume.

Subsequently, a dialysis (dialysis bag: Spectrapor, MWCO 12–14 kD) is carried out against 0.9% NaCl solution. The dialyzed material is clarified by centrifugation and filtration through a 0.2 μm filter.

The sample pretreated in this manner (2 ml aliquots) is separated on a Superdex® prep grade HR 16/60 column according to the invention and the IgA-containing fractions are isolated.

Figure 3:
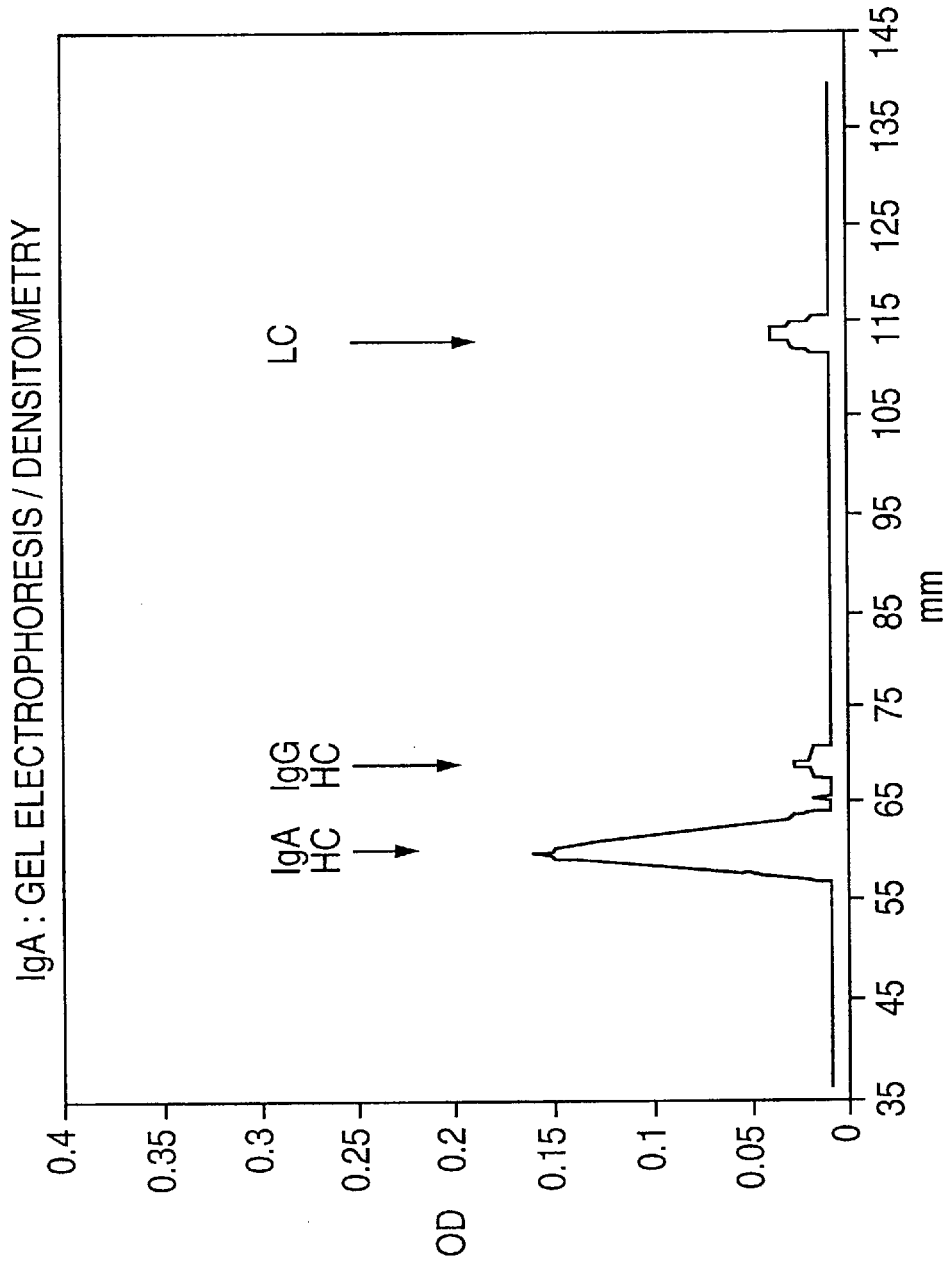

The sample isolated according to the invention is analyzed by SDS gel electrophoresis under reducing conditions (Laemmli, Nature 227 [1970] 680–685). The gel is subjected to protein staining with Coomassie Brilliant Blue and evaluated with a video densitometer (BioRad). The intensity (OD) of the bands is recorded against the separation length in the gel (mm). The main bands represent the heavy and light chains of IgA (FIG. 3 shows the desitometric evaluation of the SDS gel electrophoresis; "LC"=light chain, "HC"=heavy chain. Small amounts of the heavy chain of IgG (<10% of IgA) are observed. This residual IgG can be removed by subsequent protein G Sepharose® treatment.

The above described method allows the isolation of IgA after clarification of the starting material directly with the gel filtration methods according to the invention.

The yield of IgA with respect to the starting material (NaCl extracted paste) amounts to about 38%)

EXAMPLE 3

A pool (at least 1000 donors) of human plasma is used as a starting material for the IgA isolation.

800 ml of this plasma pool stored at −20° C. are thawed, the precipitate (cryoprecipitate) is separated and the supernatant is clarified by high speed centrifugation. The clarified supernatant is mixed with an equal volume of 14% polyethylene glycol (PEG 6000) (14% (w/v) in 0.100M Tris, 0.150M NaCl, pH 8.0), stirred for 16 h at 4° C. (the final concentration amounts to 7% PEG.) and subsequently centrifuged for 20 min (18900×g, 4° C). The supernatant is brought to a final concentration of 14% PEG with 21% (w/v) PEG 6000 in a buffer containing 0.10M Tris-HCl. 0.150M NaCl buffer, pH 6.5 and stirred again for 16 h at 4° C. and centrifuged once again (6000×g, 20 min, 4° C.). The precipitate is dissolved in 350–350 ml 0.1M Tris, 0.15M NaCl-HCl buffer (pH 8.0) and dialyzed 4×each against 5 l double distilled water (4° C., dialysis bag with 50 kilo-Dalton (kD) exclusion limit). The dialyzate is clarified by centrifugation. Precipitated material is discarded.

The supernatant of this centrifugation is brought to a final concentration of 2M ammonium sulfate with 3M ammonium sulfate, 0.040M Tris, acetic acid, pH=7.6. Then, this is stirred for 1 h at 4° C. and centrifuged once again (19,800×g, 20 min, 4° C), The precipitate is dissolved in 150–170 ml saline and dialyzed against 5 l isotonic sodium chloride in a dialysis bag with 12–14 kDalton exclusion limit two times for 16 h at 4° C. The zinc sulfate concentration in this solution is brought to 0.100M by slow addition of 2.5M $ZnSO_4$ (in distilled water) to the dialyzate. At the same time, the pH is held at 6–8 (preferably 7) by addition of 1M $Na_2CO_3$ in distilled water. Then, this is stirred for 2 h at 25° C. and centrifuged. The precipitate is discarded. The supernatant is dialyzed 3×at 4° C. against double distilled water.

This material (characterized in Table 2 as "zinc sulfate supernatant") contains about equal amounts of IgA and haptoglobin and no residual IgG.

TABLE 2

The percent distribution of IgG, IgA, IgM and haptoglobin (Hp) in the products of the individual purification steps (with respect to total protein) determined by radial immunodiffusion analysis and the yield of IgA (in % of the starting material). The ranges, determined in up to 5 separately carried out tests, are given.

| starting material | yield of IgG | IgA | IgM in % | Hp | IgA |
|---|---|---|---|---|---|
| plasma (cryosupernatant) | 11–18 | 2–4 | 0.7–2.0 | 2–4 | 100 |
| 14% PEG precipitate | 20–30 | 10–15 | up to 0.5 | 5–10 | 57–75 |
| 2 M Ammonium sulfate precipitate | 20–32 | 12–20 | up to 0.5 | 10–14 | 40–60 |
| 0.01 M zinc sulfate supernatant | 2–5 | 30–50 | up to 0.5 | 30–50 | 10–20 |
| Rivanol® supernatant | <15 | >85 | n.d. | n.d. | 4–5 |
| after Superdex® 200 | <2 | >98 | n.d. | n.d. | 2–3 | n.d. = not detectable

The dialyzed material after the zinc sulfate precipitation is brought to a final concentration of 0.1% (w/v) Rivanol® with 1% Rivanol® (6,9-diamino-2-ethoxyacridine lactate dissolved in double distilled water). In the course of the reaction, the pH decreases. With 0.010M NaOH, the pH of the mixture is held at 7.8–8.0. Subsequently, this is stirred for 1 h at room temperature and then centrifuged. The precipitate is discarded. The supernatant is dialyzed 3 to 6×at 4° C. against double distilled water. The dialyzate is concentrated by ultrafiltration (preferably in an Amicon Stir Cell equipped with Amicon YM10 membrane, Amicon, Beverly, Mass., U.S.A.).

The dialyzed Rivanol® supernatant is subjected to a batch treatment with a cation exchanger (S-Sepharose® fast flow, Pharmacia-LKB):

Pretreatment of the S-Sepharose® fast flow: 4 ml of the gel suspension are mixed with 6 ml 0.200M Tris-HCl buffer, pH 8.0, and centrifuged. The gel is washed by resuspension in 50 ml 0.010M Tris-HCl buffer, pH 8.0, and centrifugation and stored as a suspension (1 part gel, 1 part buffer) in 0.01M Tris-HCl, pH 8.0. Before use, a part of the suspension is centrifuged, the supernatant is discarded and the gel thus obtained is employed for adsorption tests:

5 ml Rivanol® supernatant is adjusted to pH 8 with 2M Tris-Base. This material is mixed with 0.5 ml S-Sepharose® fast flow gel. After 2 hours incubation at 4° C. (under shaking), the mixture is centrifuged and the supernatant is further purified by gel filtration: 2 ml aliquots of the supernatant are chromatographed using a Superdex® prep grade HR 16/60 FPLC column (Pharmacia-LKB). The IgA-containing fractions are collected and dialyzed against water. This material contains at least 98% IgA according to radial immunodiffusion analysis. IgG and haptoglobin could not be detected (<2%).

Figure 4:
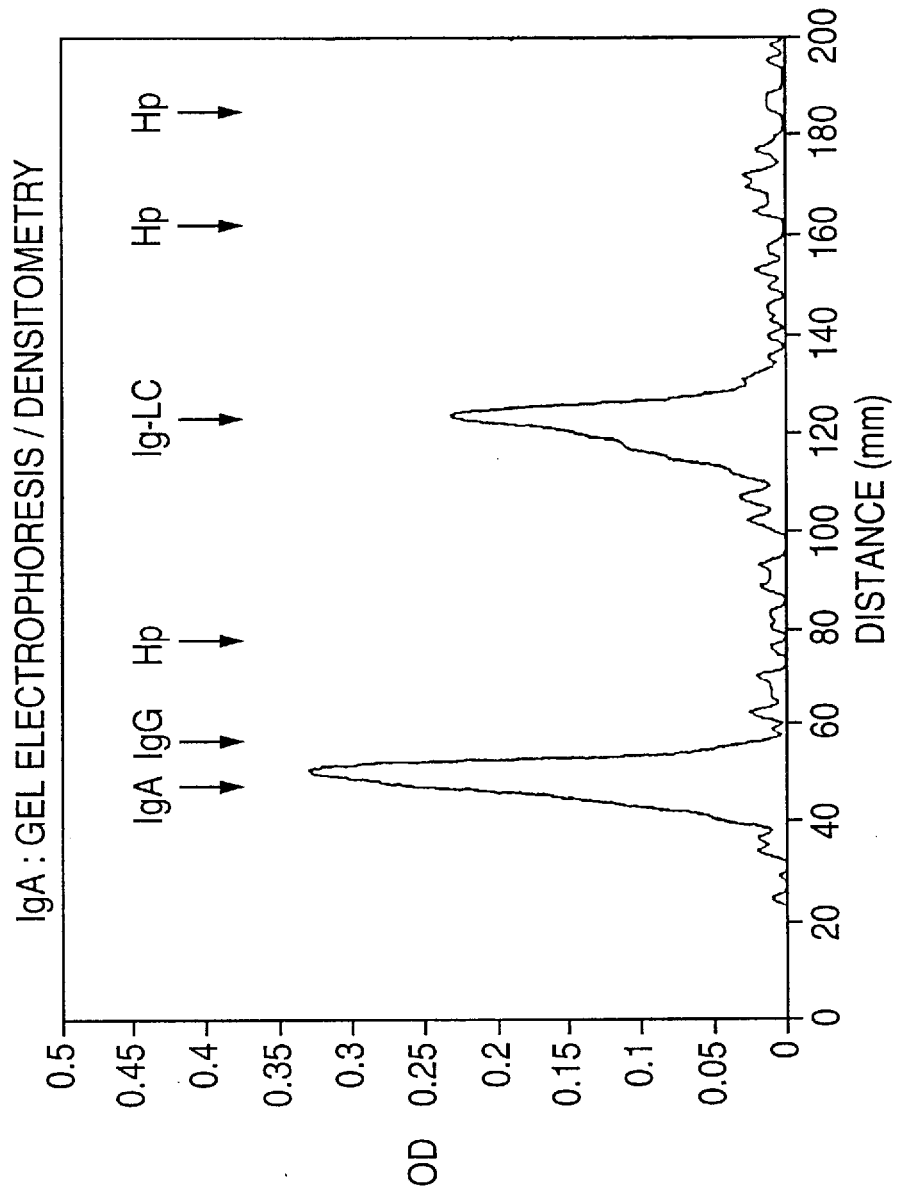

Also, SDS-polyacrylamide gel electrophoresis (reduced, according to the system of Laemmli) with subsequent densitometry (described in Example 2) only showed the bands for the heavy and the light chains of IgA (FIG. 4, "IgA" and/or "IgG" marks the positions of the heavy chains of IgA and/or IgG; "Ig-LC" and/or "Hp" mark the positions of the light chains of the immunoglobulins and/or the haptoglobin subunits).

EXAMPLE 4

As described in the patent application EP 0506 651, a Cohn fraction II+III is produced from human plasma which is extracted with a phosphate acetate buffer. This material is mixed at −2° C. with ethanol at a pH value of 5.3 to give a concentration of 12%. The precipitate formed by this procedure is removed. The supernatant is treated with an anion exchanger as described.

The anion exchange material with the bound proteins is then further treated according to the invention: 100 g paste are suspended in 1000 ml dist. water and filtered through a Buchner funnel.

The retained gel material is washed with 2 l dist. water.

The washed gel material is mixed with 300 ml 0.5M NaCl (dissolved in dist. water) and incubated for 10 min at 4° C. and then centrifuged.

The supernatant (represented in Table 3 as "NaCl extract") is kept and sterile filtered.

The extract is mixed with an equal volume of a solution of 2M ammonium sulfate, 0.1M sodium acetate, pH 6.0, and this mixture, which is now 1 molar in ammonium sulfate, is applied to a thiophilic chromatography column.

The column (type XR-16/20 from Pharmacia-LKB) is filled with 30 ml Affi-T thiophilic agarose (Kem-En-Tee, Copenhagen, Denmark) and equilibrated with a solution of 1M ammonium sulfate, 0.05M sodium acetate, pH 6.0.

The mixture is pumped over the column with a flow rate of 0.8–1.0 ml/min. Unbound proteins are washed out with 120 ml of 1M ammonium sulfate, 0.05M acetate, pH 6.0,; then, an IgA-containing fraction is eluted with 120 ml of 0.6M ammonium sulfate, 0.03M acetate, pH 6.0. Residual proteins still bound are washed out with 120 ml of 50 mM Tris, pH 8.0, before the column is re-equilibrated in 1M ammonium sulfate, 0.05M acetate.

The fraction eluted with 0.6M ammonium sulfate is dialyzed 3×against dist. water in a dialysis bag with a cut-off of 50 kD.

The dialyzed material (presented in Table 3 as "ammonium sulfate eluate" is concentrated by centrifugation to about 3 mg/ml and then chromatographed over a gel filtration column (Superdex® S200 prep grade HR 35/600, Pharmacia-LKB) in 10 ml aliquots.

The IgA-containing fractions are collected, pooled and dialyzed against PBS several times.

The yield of IgA, as compared to the IgA content of the "NaCl extract", amounted to about 22–30% (Table 3).

Figure 5:
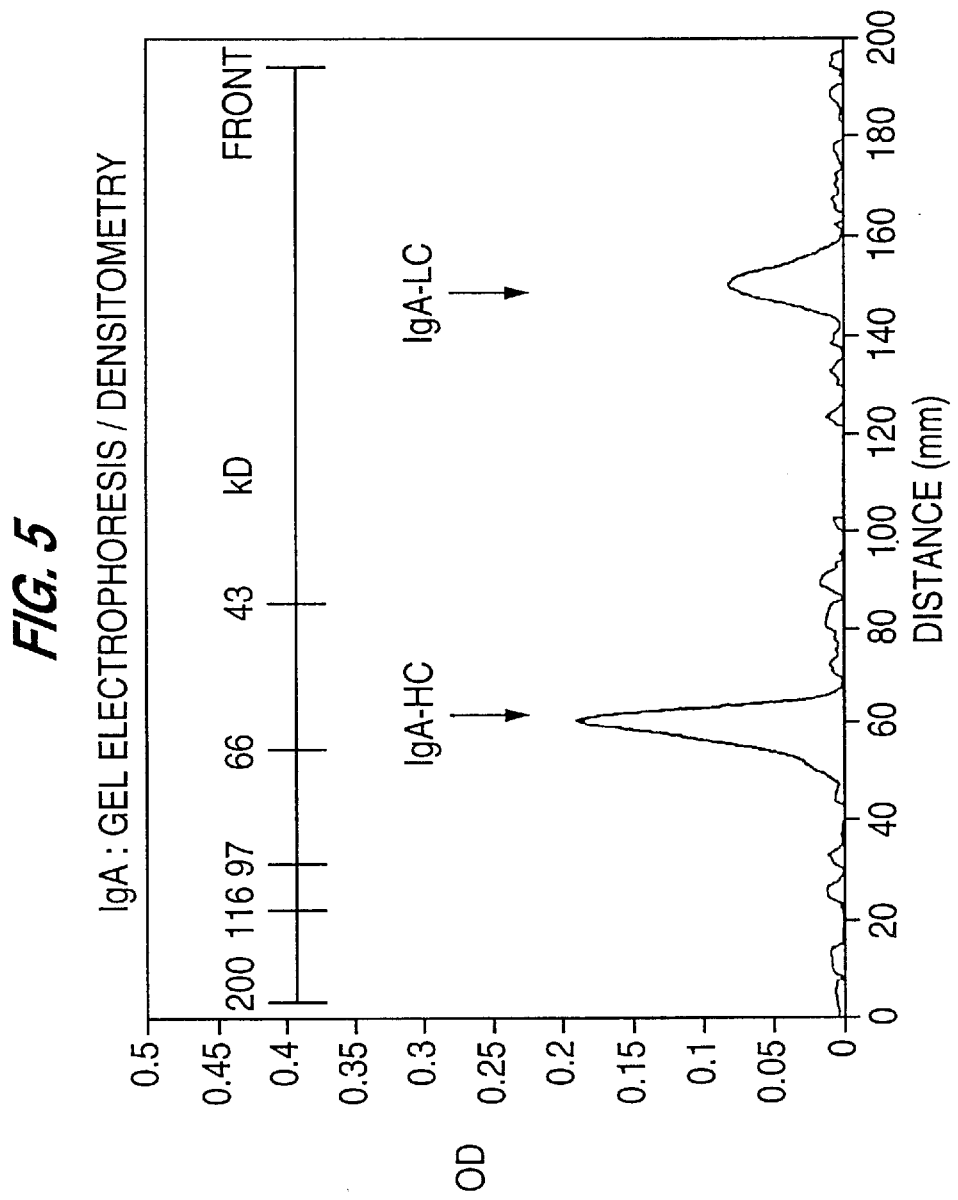

The material purified according to the invention consists of up to 95% IgA, as was measured by radial immunodiffusion analysis (Table 3). FIG. 5 shows the SDS-polyacrylamide gel electrophoresis of the reduced samples according to the Laemmli system and subsequent densitometry (description in Example 2) of the gel. Only the characteristic bands for the heavy ("IgA-HC") and the light ("IgA-LC") chains of the IgA are recognizable.

IgA with a purity of >99% can be isolated by a further treatment with protein G Sepharose® fast flow (Pharmacia-LKB) in batch process.

The amount of protein G Sepharose® fast flow is to be adjusted thereby such that 1 ml of gel material is present per 10 mg IgG still contained in the batch. After 3–6 hour incubation with shaking, the protein G Sepharose® with the IgG bound thereto is separated by centrifugation. The supernatant is dialyzed against distilled water.

Figure 6:
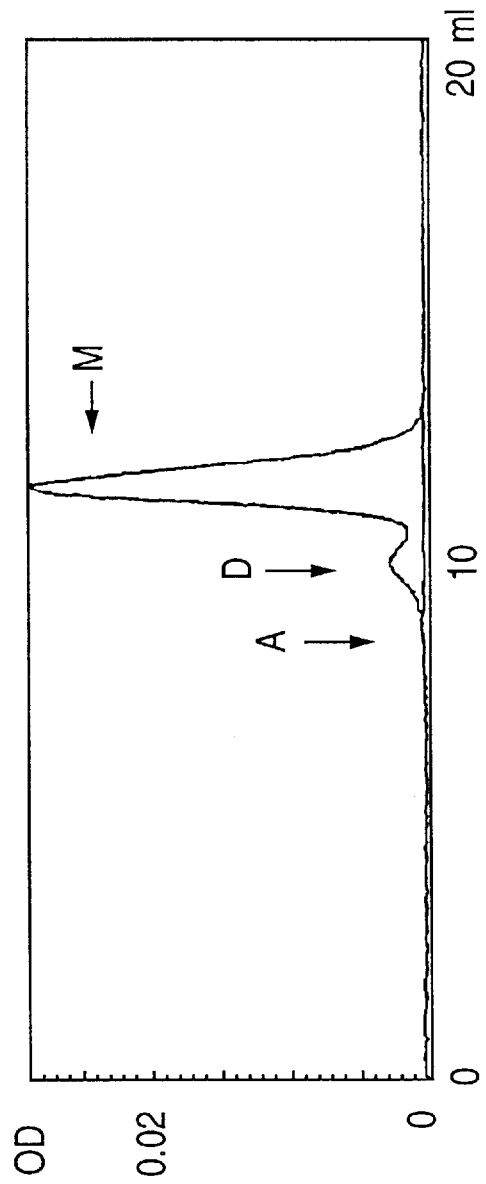

This end product was also analyzed on an analytical Superdex® HR 10/30 gel filtration column (method description in Example 1). It consists for the most part of IgA monomers with small amounts (5–10%) IgA dimers (FIG. 6; "D"=IgA dimers, "M"=IgA monomers, "A"=aggregates). IgA aggregates are present, if at all, in an amount of <2%. In the end product produced according to the invention, no IgG can be detected by radial immunodiffusion. Based on the sensitivity limits of the methods applied, this means that less than 1% IgG is present in the IgA preparation.

TABLE 3

The distribution of IgG and IgA in the products of the individual purification steps (given in percent of total protein), determined by radial immunodiffusion analysis, and the yield of IgA (in % of the starting material). The ranges found in 4 separately carried out purification procedures are given.

|  | % IgG | % IgA | % IgA yield |
|---|---|---|---|
| NaCl extract | 6–9 | 17–26 | 100 |
| ammonium sulfate eluate | 5–12 | 70–85 | 35–47 |
| after Superdex ® 200 | 4–9 | 91–95 | 22–30 |
| end product | n.d. | >99 | 18–25 | n.d. = not detectable

EXAMPLE 5

The IgA subclass composition and the distribution of kappa and lambda light chains in the purified preparations The IgA preparations according to the invention produced in Examples 1, 3 and 4 were tested for their IgA subclass distribution with the aid of radial immunodiffusion plates (The Binding Site, Birmingham, England) (method according to the instructions of the supplier) and compared with a plasma pool (prepared from more than 1000 healthy, adult blood donors): the distribution of the IgA subclasses in the products produced according to the invention hardly differs from that of normal plasma (Table 4).

The light chain composition of the purified IgA was examined with radial immunodiffusion plates obtained from Behring (Marburg, Germany, method according to the instructions of the firm Behring). No difference in the kappa:lambda ratio between purified IgA and a standard plasma pool (in which the kappa:lambda ratio of all immunoglobulin classes was measured) could be observed (Table 5).

These results show that the IgA produced according to the invention corresponds in its composition to the IgA contained in serum.

TABLE 4

The IgA subclass distribution of the purified IgA preparations measured by radial immunodiffusion.

|  | % IgA1 | % IgA2 |
|---|---|---|
| plasma pool | 79 | 21 |
| IgA from example 1 | 78 | 22 |
| IgA from example 3 | 76 | 24 |
| IgA from example 4 | 75 | 25 |

TABLE 5

The light chain composition of purified IgA measured by radial immunodiffusion (evaluation in units/dl)

|  | kappa/lambda |
|---|---|
| plasma pool | 0.99 |
| IgA from example 3 | 0.95 |

EXAMPLE 6

Testing of the biological effectiveness of the purified IgA preparations

The capability of the IgA products to recognize and bind bacteria after their purification according to the invention was examined in a test system:

20 µl aliquots are taken from an *E. coli* suspension (Nr COPO54, $1.39 \times 10^{10}$/ml) and suspended in 1.4 ml of the IgA produced according to the invention (1 mg/ml) and/or in 1.4 ml human plasma pool (1 mg/ml IgA) as a control. 0.100 ml of a 1% (w/v) solution of bovine serum albumin in PBS (abbreviated in the following as PBS/BSA) is added. This is incubated for 60 min at 4° C. with occasional shaking. Then, this is centrifuged (Eppendorf, 12000 rpm, 5 min, 4° C.) and the bacteria are washed 4 times, each time with 1 ml PBS/BSA. The bacteria are resuspended in 0.5 ml PBS/BSA. Then, suspensions are mixed with 20 µl of a fluorescence-labeled anti-human-IgA antibody (fluorescein (DTAF) conjugated affi pure rabbit F(ab)2 anti-human IgA (alpha chain spec.), Jackson ImmunoResearch, West Grove, Pa., U.S.A.) and incubated for 60 min at 4° C. with occasional shaking. Then, the bacterial suspensions are washed 4 times, each time with 1 ml PBS/BSA, and subsequently suspended in 0.5 ml PBS/BSA. The binding of IgA and fluorescence-labeled anti-human-IgA on the bacteria is measured with a fluorescence activated cell sorter (type: FACStar-Plus, Becton Dickinson, Mountain View, Calif., U.S.A.).

Bacteria which were incubated with the fluorescence-labeled antibody, but not with the IgA-containing product (but instead with pure PBS) serve as a blank. The analysis shows (FIG. 7, the x-axis defines the intensity of the fluorescence and the y-axis the number of the detected bacteria) that the IgA isolated according to the invention binds equally well to bacteria as the IgA from the plasma pool. 74% of the bacteria which were incubated with plasma IgA and 77% of the bacteria which were incubated with IgA purified according to the invention bound IgA.

These results show that the biological function of the IgA, to bind to certain bacteria, is also maintained after the purification according to the invention.

EXAMPLE 7

Lyophilization and heat treatment of the isolated IgA for the inactivation of possibly present viral contaminants 4 ml of an IgA with an IgA concentration of 10 mg/ml produced according to the invention are lyophilized. Subsequently, the freeze-dried material is moistened in the lyophilization vial (by addition of 7% water in comparison to the total weight of the sample). Thereafter, the tightly sealed vials are heat treated for 10 h at 60° C. and subsequently for 1 h at 80° C.

Figure 8:
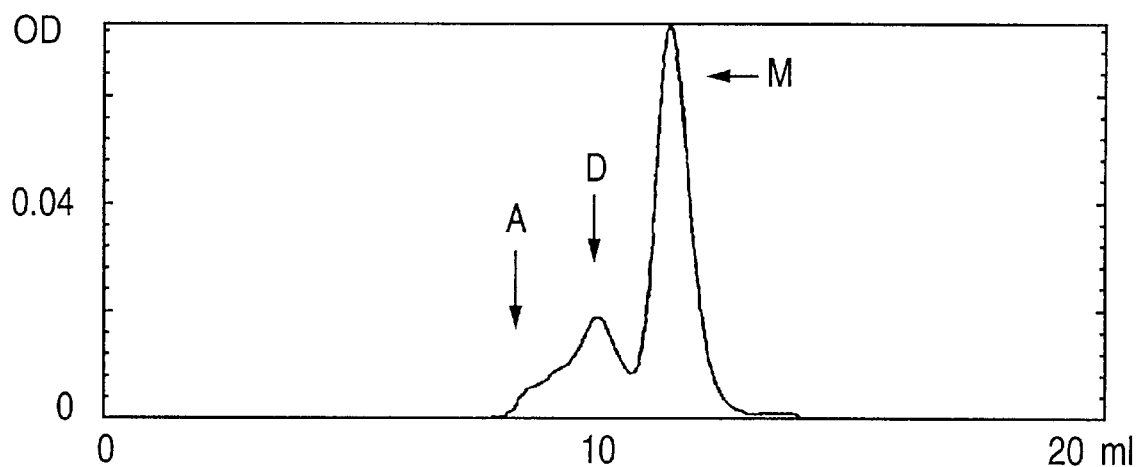

The heat treated samples are reconstituted with PBS to the starting volumes and the solutions obtained in this manner are analyzed by gel filtration (described in Example 1) with a Superdex® S200 HR 10/30 FPLC column. FIG. 8 ("M"= IgA monomers, "D"=IgA dimers, "A"=aggregates) shows that after lyophilization and heat treatment the IgA still consists of more than 96% IgA monomers.

EXAMPLE 8

Heat treatment of dissolved IgA

IgA isolated according to the invention is dissolved in distilled water in a concentration of 0.4 mg/ml and incubated for various times in a water bath at different temperatures.

Subsequently, the material is analyzed with a Superdex® 200 HR 10/30 gel filtration column as described in Example 1.

Figure 9:
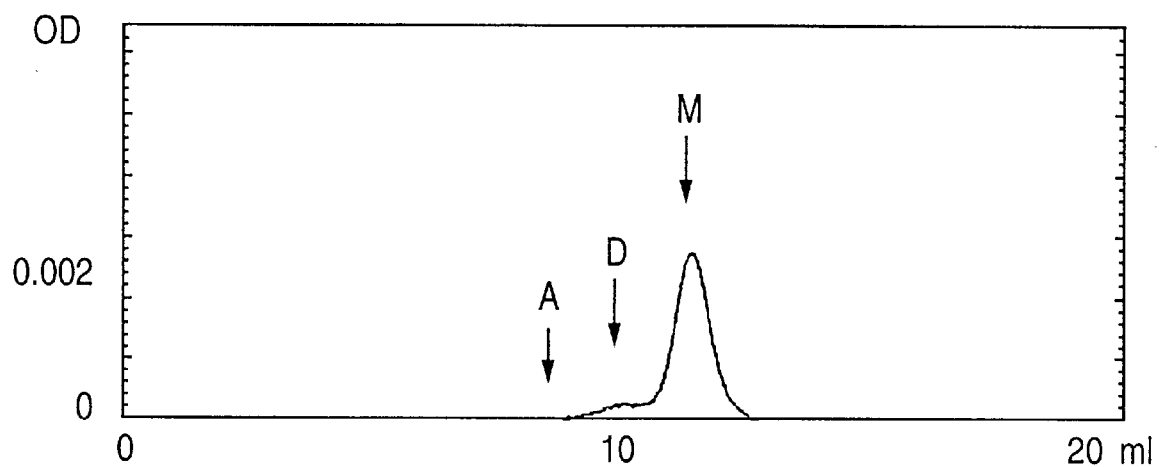
Figure 10:
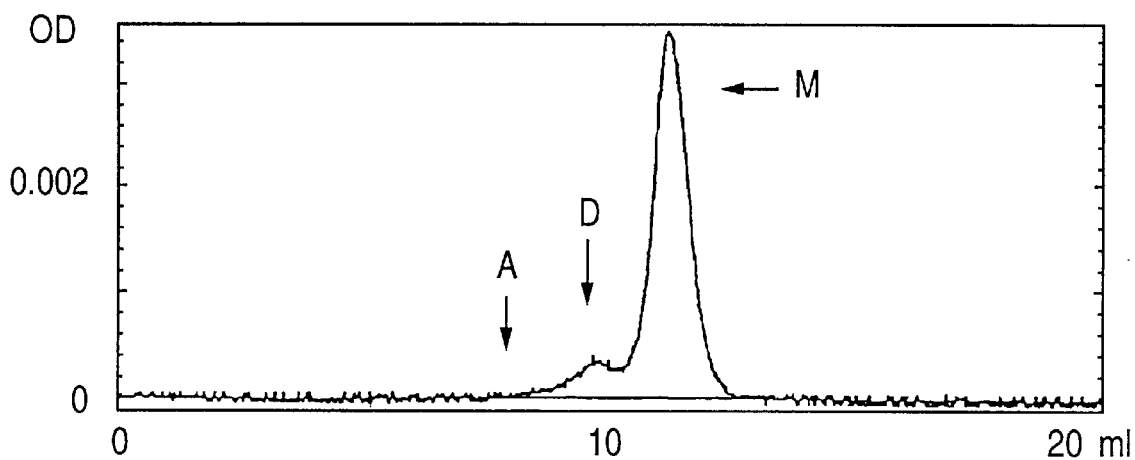
Figure 11:
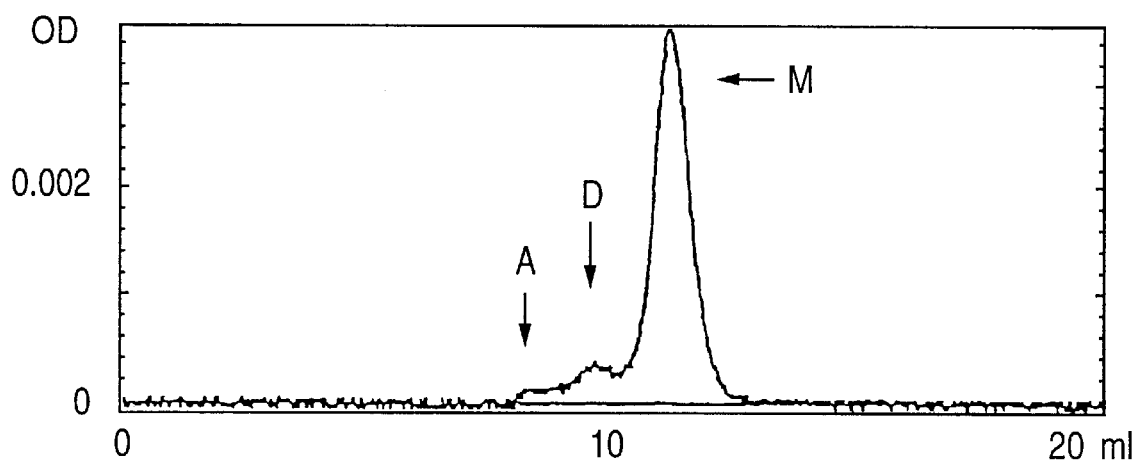

The comparison with an untreated IgA preparation (see FIG. 2 or FIG. 6) shows that neither heating to 60° C. for 30 min (FIG. 9) nor heating to 40° C. for 8 hours results in aggregate formation. Even after heating for 8 hours at 40° C. and subsequently for 8 hours at 50° C. (FIG. 11), less than 2% aggregates are observed. In the FIGS. 9–11, "M", "D" and/or "A" represent the positions of the IgA monomers, IgA dimers and/or aggregates.

EXAMPLE 9

In order to test the influence of hydrophilic/hydrophobic and/or electrostatic interactions with the column materials, a sample consisting essentially of IgA and IgG is analyzed with equally dimensioned gel filtration columns filled with different gel material. For this, equally large aliquots are applied to the columns and eluted isocratically under identical elution conditions (0.5 ml/min).

Figure 12:
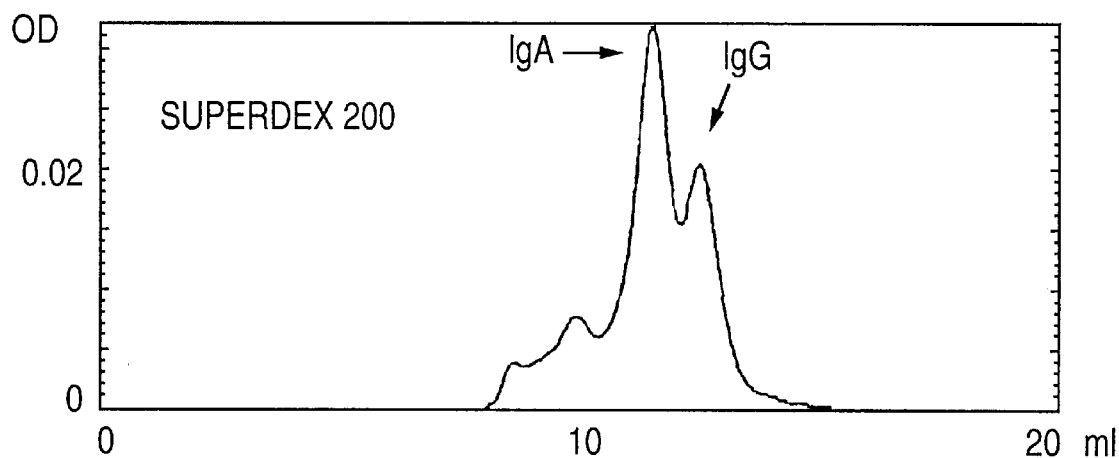
Figure 13:
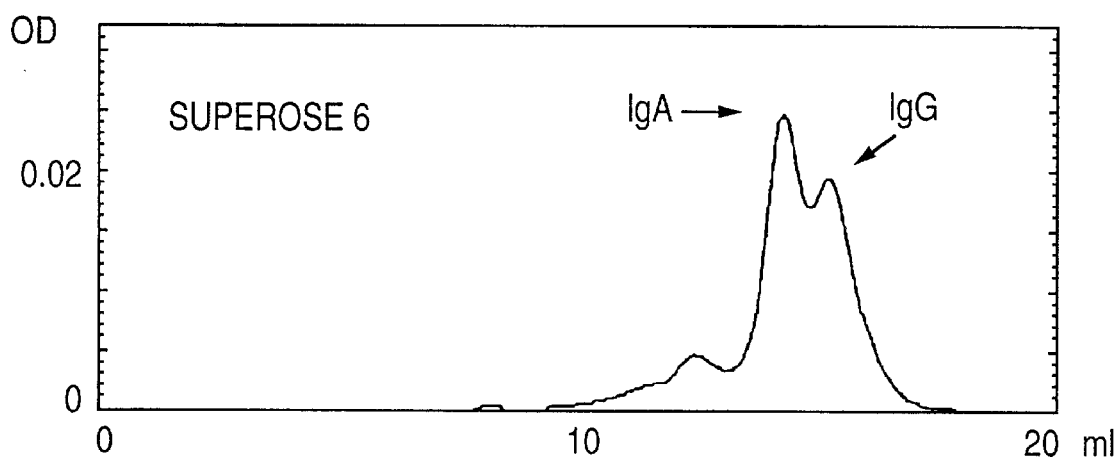

The following analyses were carried out with gel filtration columns which were equilibrated with phosphate buffered 0.15M NaCl solution (flow rate: 0.5 ml/min, measurement of the optical density (OD) at 280 nm):

IgG and IgA were separated in the same way on a Superdex® 200 HR 10/30 column (Pharmacia-LKB) (FIG. 12) as on a Superose® 6 HR 10/30 column (Pharmacia-LKB) (FIG. 13).

Figure 14:
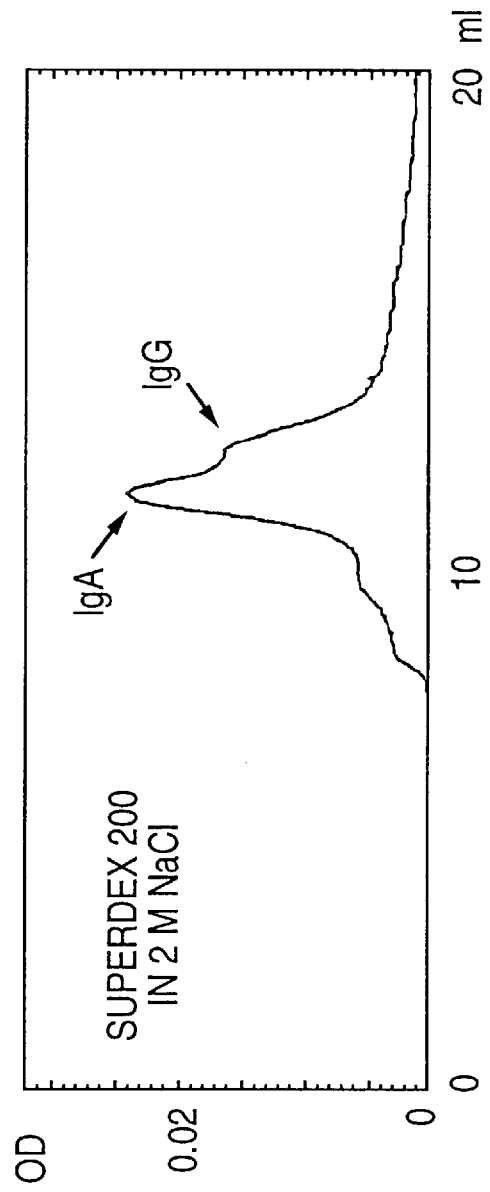

In contrast, when the gel filtration is carried out under conditions of high ionic strength (2M NaCl), separation is no longer possible on the Superdex® HR 10/30 column because protein peaks migrate more closely (FIG. 14). This result indicates that the separation of IgA and IgG on Superdex® 200 not only depends on the difference in molecular weight (IgA: 162 kD, IgG: 153 kD [Heremans J. F., Immunoglobulin IgA, in The Antigens, vol. 2 (1974) p.

365–522; Academic Press, New York]), but also on the different hydrophobic and/or electrostatic interactions of IgG and IgA with the column material.

We claim:

1. Virus-safe human monomeric IgA essentially free of IgG obtainable by
    (a) providing an immunoglobulin-containing fraction from serum, plasma or a plasma fraction,
    (b) purifying the immunoglobulin-containing fraction to obtain monomeric IgA that is essentially free of IgG, and
    (c) treating the monomeric IaA to inactivate viruses.

2. Monomeric IgA according to claim 1, wherein the purifying is performed by at least one chromatographic method.

3. Monomeric IgA according to claim 1, wherein the treating step comprises at least one of heat treatment, UV radiation, solvent detergent, tensides or peptide hydrolases.

4. Monomeric IgA according to claim 1, wherein the IgA comprises IgA1 and IgA2 in a native composition.

5. Monomeric IgA according to claim 1, wherein the IgA is free of fibrinogen.

6. Monomeric IgA according to claim 1, wherein the IgA is free of plasminogen.

7. Stable pharmaceutical preparation according to claim 1 consisting essentially of human monomeric IgA.

8. Method for the production of virus-safe monomeric IgA, which comprises the following steps:
    (a) purification of an immunoglobulin containing fraction such that a monomeric IgA essentially free of IgG is obtained and
    (b) carrying out a process for the inactivation of viruses.

9. Method according to claim 8, wherein the purifying is performed by at least one chromatographic method.

10. Method according to claim 8, wherein the process of step (b) comprises at least one of heat treatment, UV radiation, solvent detergent, tensides or peptide hydrolases.

11. Method according to claim 8, wherein the immunoglobulin-containing fraction is selected from the group consisting of human serum, plasma and plasma fractions.

12. Method according to claim 8, wherein the immunoglobulin-containing fraction is from a Cohn II+III fraction.

13. Method according to claim 9, wherein at least one chromatographic method is selected from the group consisting of gel permeation chromatography, thiophilic chromatography, affinity chromatography and ion exchange chromatography.

14. Method according to claim 9, wherein at least one chromatographic method relies upon at least one of hydrophilic, hydrophobic or electrostatic interactions.

15. Method according to claim 10, wherein the heat treatment is carried out between 40° C. to 80° C.

16. Method according to claim 15, wherein prior to heat treatment the monomeric IgA is dialyzed against water.

17. Method for the production of a preparation comprising monomeric IgA essentially free of IgG, comprising adsorbing plasma or a plasma fraction to a thiophilic matrix, and then eluting the monomeric IgA from the matrix.

18. A method of producing a virus-safe purified monomeric IgA preparation that is essentially free of IgG, comprising
    purifying monomeric IgA from an immunoglobulin-containing fraction to obtain a purified preparation comprising monomeric IgA that is essentially free of IgG; and
    treating the purified preparation to inactivate viruses, thereby yield the virus-safe purified monomeric IgA preparation that is essentially free of IgG.

19. The method according to claim 18, wherein the treating comprises heating the purified preparation to a temperature between about 40° C. to about 80° C.

20. The method according to claim 19, wherein the treating is carried out in the absence of stabilizers.

21. The method according to claim 19, wherein the purified preparation comprises a non-precipitating amount of a polyether or polyhydroxyether during the heating.

22. The method according to claim 18, wherein the purifying employs at least one of gel permeation chromatography, thiophilic chromatography and affinity chromatography.

23. The method according to claim 18, wherein the treating comprises exposing the purified preparation to at least one of UV radiation, solvent detergent, tensides or peptide hydrolases.

24. The method according to claim 18, wherein the immunoglobulin-containing fraction is obtained from serum, plasma, a plasma fraction or colostrum.

25. The method according to claim 18, wherein the virus-safe purified preparation is free of at least one of fibrinogen and plasminogen.

26. Virus-safe, purified monomeric IgA preparation that is essentially free of IgG, produced by
    purifying monomeric IgA from an immunoglobulin-containing fraction to obtain a purified preparation comprising monomeric IgA that is essentially free of IgG; and
    treating the purified preparation to inactivate viruses, thereby yield the virus-safe, purified monomeric IgA preparation that is essentially free of IgG.

27. The preparation according to claim 26, wherein the treating comprises heating the purified preparation to a temperature between about 40° C. to about 80° C.

28. The preparation according to claim 26, wherein the treating comprises exposing the purified preparation to at least one of UV radiation, solvent detergent, tensides or peptide hydrolases.

29. The preparation according to claim 26, wherein the immunoglobulin-containing fraction was obtained from serum, plasma, a plasma fraction, colostrum or Cohn II+III fraction.

30. The preparation according to claim 26, wherein the preparation is free of at least one of fibrinogen and plasminogen.

* * * * *

UNITED STATES PATENT AND TRADEMARK OFFICE
CERTIFICATE OF CORRECTION

PATENT NO. : 5,808,000
DATED : 9/15/98
INVENTOR(S) : Mannhalter et al.

It is certified that error appears in the above-identified patent and that said Letters Patent is hereby corrected as shown below:

Column 8, line 15, delete "Fig 7" and insert --Figs 7A-7C--.

Column 15, line 64, delete "Fig 7" and insert --Figs 7A-7C--.

Signed and Sealed this

Twenty-third Day of February, 1999

Attest:

Q. TODD DICKINSON

*Attesting Officer*         *Acting Commissioner of Patents and Trademarks*